United States Patent [19]
Matsuno

[11] Patent Number: 5,766,189
[45] Date of Patent: Jun. 16, 1998

[54] CLIP DEVICE

[75] Inventor: Kiyotaka Matsuno, Hachioji, Japan

[73] Assignee: Olympus Optical Co., Ltd., Tokyo, Japan

[21] Appl. No.: 805,822

[22] Filed: Feb. 26, 1997

[30] Foreign Application Priority Data

Feb. 29, 1996 [JP] Japan .................................. 8-042468
Oct. 14, 1996 [JP] Japan .................................. 8-270464

[51] Int. Cl.$^6$ .................................................. A61B 17/08
[52] U.S. Cl. ........................ 606/158; 606/151; 606/157; 606/142; 606/139
[58] Field of Search ............................ 606/151, 158, 606/157, 139, 142, 143; 227/901, 902

[56] References Cited

U.S. PATENT DOCUMENTS

| | | | |
|---|---|---|---|
| 3,867,944 | 2/1975 | Samuels | 128/325 |
| 4,367,746 | 1/1983 | Derechinsky | 128/325 |
| 4,765,335 | 8/1988 | Schmidt et al. | 128/326 |
| 5,201,746 | 4/1993 | Shichman | 606/151 |
| 5,217,473 | 6/1993 | Yoon | 606/157 |
| 5,366,459 | 11/1994 | Yoon | 606/151 |
| 5,520,701 | 5/1996 | Lerch | 606/142 |
| 5,569,274 | 10/1996 | Rapacki et al. | 606/158 |

FOREIGN PATENT DOCUMENTS

| | | | |
|---|---|---|---|
| 4319829C1 | 8/1994 | Germany . | |
| 4102450 | 3/1992 | Japan | 606/151 |
| 426091 U | 6/1992 | Japan . | |

*Primary Examiner*—Michael Buiz
*Assistant Examiner*—Tina T. D. Pham
*Attorney, Agent, or Firm*—Kenyon & Kenyon

[57] ABSTRACT

A clip device for a living tissue in a body cavity includes an introducing tube insertable into the body cavity. An operating member of the device is advanceably and retreatably inserted into the introducing tube; the operating member has a distal end portion. An operating wire is advanceably and retreatably inserted into the operating member, and the operating wire has a distal end portion and a retainer attached to the distal end portion of the operating wire. The clip device further includes a clip having a proximal end portion and a pair of arm portions extending from the proximal end portion and provided with a tendency to open. A clip squeezing ring is removably attached to the distal end portion of the operating member for closing the arm portions of the clip by fitting to the arm portions of the clip. And a coupling member is insertable into the clip squeezing ring, and the coupling ring is removably engaged with the retainer. The coupling ring further includes a hook portion to be engaged with the proximal end portion of the clip; holding member holds the coupling member inside the clip squeezing ring such that the coupling member can be removed from the clip squeezing ring when the operating wire is retreated. At least one of the arm portions is bent inward so as to be bow-shaped, and has an inner side provided with friction increasing the structure for increasing friction between the inner side of the arm portion and the living tissue.

14 Claims, 5 Drawing Sheets

5,766,189

CLIP DEVICE

BACKGROUND OF THE INVENTION

1. Field of the Invention

This invention relates to a clip device used for hemostasis, marking, and ligation of a living tissue in a body cavity.

2. Description of the Related Art

Conventionally, a clip is introduced into a body cavity via an endoscope to grasp a living tissue of a body cavity for hemostasis, marking, and ligation, and the clip is left inside the body cavity. A device for such treatment is disclosed in, for example, Japanese Published Utility Model Application Publication No. Hei 4-26091.

Japanese Published Utility Model Application Publication No. Hei 4-26091 describes a clip device for grasping a living tissue. The clip device comprises a clip having a pair of grasping portions provided with a tendency to open; a clip squeezing ring for pulling in and closing the clip; and a coupling member insertable into the clip squeezing ring and provided with a deformable hook portion to be engaged with the clip. The clip and the coupling member are temporarily retained inside the clip squeezing ring by inserting them into the clip squeezing ring and filling a filler made of silicone. Further, the coupling member can be engaged with and disengaged from the main body of the device which has a guide tube insertable into a body cavity through an endoscope.

Japanese Laid-Open Patent Application Publication No. Hei 5-212043 discloses a clip device having a pair of grasping portions provided with a tendency to open, each of the grasping portions being provided in its middle with a bent portion bent outward in order to reduce the gap between the grasping portions.

However, because the clip and the coupling member of the clip device disclosed in Japanese Published Utility Model Application Publication No. Hei 4-26091 are temporarily retained inside the clip squeezing ring by the filler, the force for fixing the members may vary in accordance with the state of filling the filler. Thus, the members may be separated by the handling of the device before the clip is left on the living tissue. Additionally, because silicone is used as the filler of the clip device as described above, the assembly of the device is not easy. Further, because silicone is expensive, the clip device is also expensive. On the other hand, Japanese Laid-Open Patent Application Publication No. Hei 5-212043 describes that the gap between the grasping portions of the clip is reduced to ligate a polyp or a blood vessel. However, the grasping portions of the clip cannot reliably grasp the living tissue, because the tissue slips from the inner surfaces of the grasping portions. Further, if the end portions of the clip are shaped sharply, the tissue will be injured during the ligation.

SUMMARY OF THE INVENTION

An object of this invention is to provide a clip device which can simplify the handling of a clip before it is left on a living tissue, and can reliably grasp the tissue to be treated, and will not injure the tissue during the treatment.

In order to attain the above object, a clip device for a living tissue in a body cavity according to this invention comprises an introducing tube insertable into the body cavity. An operating member of the clip device is advanceably and retreatably inserted into the introducing tube; the operating member has a distal end portion; An operating wire is advanceably and retreatably inserted into the operating member, and the operating wire has a distal end portion and a retainer attached to the distal end portion of the operating wire. The clip device further includes, a clip having a proximal end portion and a pair of arm portions extending from the proximal end portion and provided with a tendency to open. A clip squeezing ring is removably attached to the distal end portion of the operating member for closing the arm portions of the clip by fitting to the arm portions of the clip. A coupling member is insertable into the clip squeezing ring, and the coupling ring is removably engaged with the retainer. The coupling ring further includes a hook portion to be engaged with the proximal end portion of the clip. A holding member holds the coupling member inside the clip squeezing ring such that the coupling member can be removed from the clip squeezing ring when the operating wire is retreated. At least one of the arm portions is bent inward so as to be bow-shaped, and has an inner side provided with friction increasing structure for increasing friction between the inner side of the arm portion and the living tissue.

Other characteristics and advantages of this invention will be apparent from the following description.

DETAILED DESCRIPTION OF THE PREFERRED EMBODIMENTS

Figure 2A:
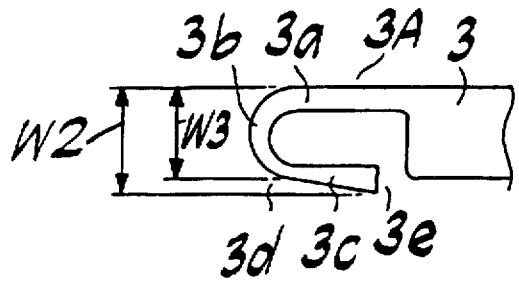
FIG. 2(A) is an illustration showing a shape of a hook portion of a coupling plate.
Figure 2B:
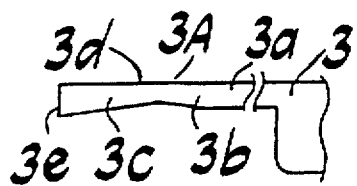
FIG. 2(B) is an illustration showing a deformed state of the hook portion of the coupling plate.
Figure 3:
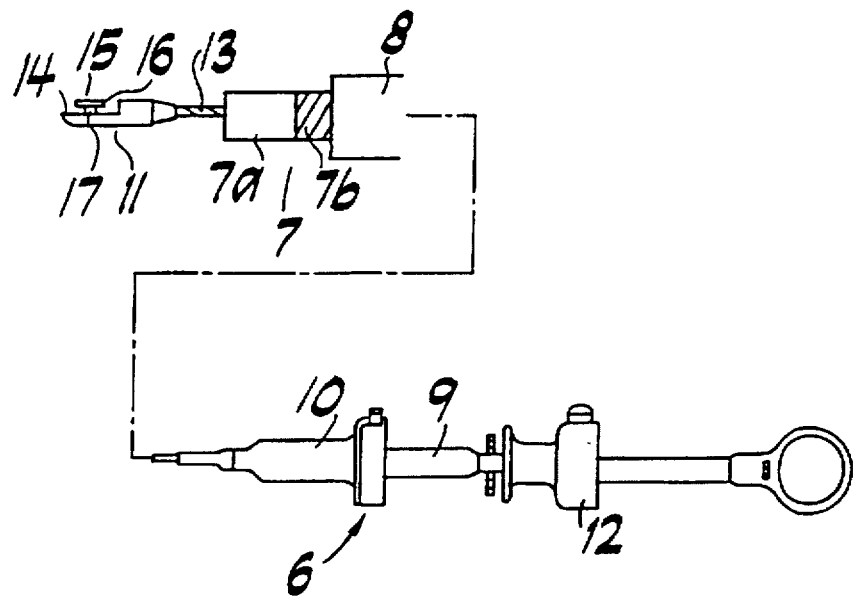
FIG. 3 is an illustration showing the structure of a clip operating device as a whole.

Referring to FIGS. 1 to 8, a first embodiment of this invention will be described. A clip device of the first embodiment comprises a cassette-type clip unit 1 as shown in FIG. 1, and a clip operating device 6 as shown in FIG. 3.

The clip unit 1 has a clip 2, a coupling plate 3 to be used as a coupling member, and a holding tube 4 to be used as a clip squeezing ring.

The clip 2 is formed by a metallic plate, such as a leaf spring, which is bent at its center. Further, as shown in FIG.

1(B), the metallic plate intersects near the bent portion, and a pair of arm portions 2A and 2B having a tendency to open extend with their distal end portions separating from each other. On the proximal end side of the clip 2 a substantially oval-shaped proximal end portion 2d is formed.

Figure 1A:
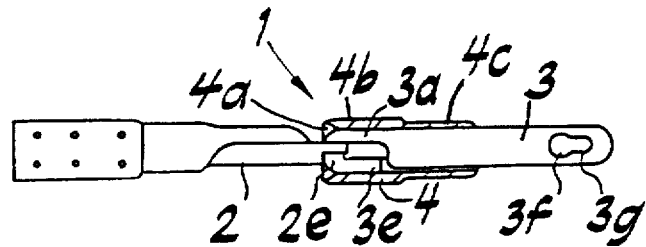
FIG. 1(A) is a plane view of a clip.
Figure 1B:
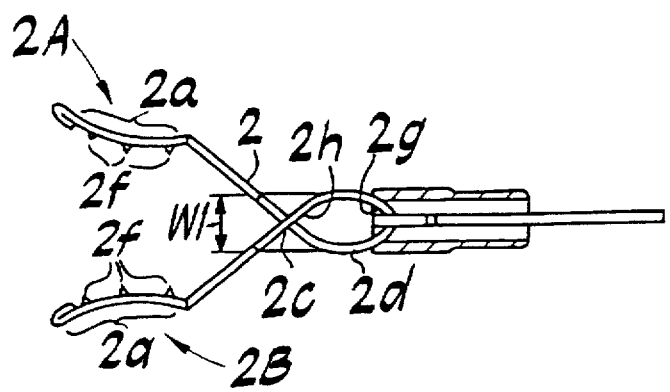
FIG. 1(B) is a side view of the clip shown in FIG. 1(A).

As shown in FIG. 1(A), the proximal end portion 2d of the clip 2 comprises a proximal curved portion 2g provided with a recess 2e. As shown in FIG. 1(B), the curved portion 2g has a smaller radius of curvature than that of a curved portion 2h on the side of an intersecting portion 2c. The width WI of the oval portion of the proximal end portion 2d is larger than the inside diameter of the holding tube 4.

Figure 1C:
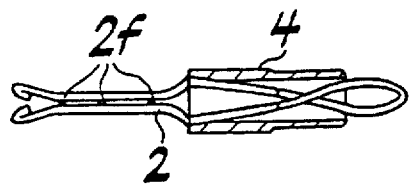
FIG. 1(C) is a side view showing the closed state of the arm portions of the clip.

Further, the arm portions 2A and 2B each are provided with a bow-shaped portion 2a which is bent inward so as to decrease the gap between the arm portions 2A and 2B when they are closed. The inner side of the bow-shaped portion 2a is provided with protrusions 2f. The number of the protrusions 2f is preferably 4 to 8. The protrusions 2f of the arm portion 2A are positioned so as to abut on or be interposed between those of the arm portion 2B when the arm portions 2A and 2B are closed. Because the distal end portions of the arm portions 2A and 2B are folded back towards the proximal end side of the clip, the distal end portions of the clip 2 are obtuse. As shown in FIG. 1(C), when the arm portions 2A and 2B are closed, the whole bow-shaped portions 2a contact almost closely with each other owing to their elasticity.

The coupling plate 3 is formed by photoetching or by pressing a metallic plate. As shown in FIG. 2(A), the coupling plate 3 is provided in its distal end portion with a hook portion 3A. The hook portion 3A is hooked on the recess 2e of the clip 2 to removably engage with the clip 2. The hook portion 3A comprises a straight portion 3a extending from a main body of the coupling plate 3 toward its distal end, an arc portion 3b extending from the strait portion 3a and forming a semicircle shape which turns to the proximal direction, and an inclined portion 3c further extending from the arc portion 3b towards the proximal direction.

The width of the hook portion 3A from the straight portion 3a to the middle portion of the arc portion 3b is approximately the same. From the middle portion of the arc portion 3b to a boundary portion 3d between the arc portion 3b and the inclined portion 3c, the width gradually becomes narrow. That is, the width of the hook portion 3A is the narrowest at the boundary portion 3d. Further, the inclined portion 3c is formed so that it widens towards the outside of the hook portion 3A from the boundary portion 3d to an end portion 3e. Thus, as shown in FIG. 2(A), the width W2 of the coupling plate 3 at the end portion 3e is the widest.

Figure 4:
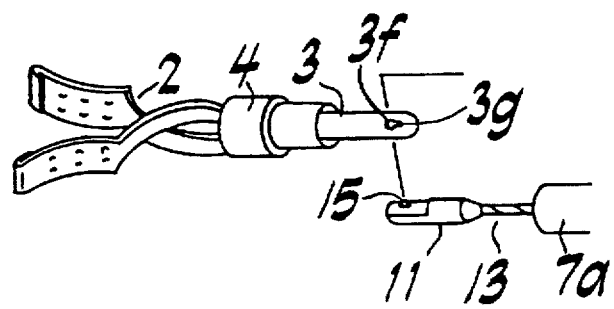
FIG. 4 is an illustration showing the coupling of the clip unit with the retainer of the clip operating device.

As shown in FIG. 1(A), the proximal end side of the coupling plate 3 is provided with a large-diameter opening 3f and a small-diameter opening 3g connected with the large-diameter opening 3f. As shown in FIG. 4, the large-diameter opening 3f and the small-diameter opening 3g are engaged with a pin 15 provided to the distal end portion of the clip operating device 6 so that the coupling plate 3 is coupled to the clip operating device 6.

As shown in FIG. 1(A), the holding tube 4 is substantially cylindrical and provided with a tapered portion 4a on the distal end side of its hollow portion. The outside shape of the holding tube 4 is formed by a large-diameter portion 4b on the distal end side of the holding tube 4, and a small-diameter portion 4c. As shown in FIG. 2(A), the maximum width W2 of the coupling plate 3 is larger than the inner diameter of the holding tube 4. However, the width W3 of the coupling plate 3 at the boundary portion 3d is smaller than the inner diameter of the holding tube 4.

The respective members are assembled in the following manner to construct the clip unit. The hook portion 3A of the coupling plate 3 is inserted through the substantially oval-shaped proximal end portion 2d of the clip 2 and hooked on the recess 2e. In this state, the proximal end portion of the coupling plate 3 is inserted into the hollow of the holding tube 4 from its distal end side. Because the coupling plate 3 is longer than the holding tube 4, the proximal end portion of the coupling plate 3 protrudes from the proximal end portion of the holding tube 4.

The proximal end portion of the coupling plate 3 protruding from the holding tube 4 is held, and the coupling plate 3 is further pulled in the holding tube 4 until the clip 2 contacts the distal end portion of the holding tube 4, so that the hook portion 3A is elastically deformed by the tapered portion 4a of the holding tube 4 gradually. That is, the maximum width W2 of the coupling plate 3 at the end portion 3e of the hook portion 3A is gradually reduced, and the end portion 3e generates an urging force that presses against the tapered portion 4a of the holding tube 4. The hook portion 3A is elastically deformed by being bent inward from the boundary portion 3d which has the narrowest width, that is, the smallest cross-sectional area of the hook portion 3A.

After a while the end portion 3e passes the tapered portion 4a and reaches the inner wall of the holding tube 4 to press the inner wall. In this state, the coupling plate 3, which is provided with a sufficient resilient force due to the deformation of the hook portion 3A is temporarily held inside the holding tube 4, and the respective parts constructing the clip unit 1 are temporarily fixed and retained. The amount of the resilient force caused by the deformation of the hook portion 3A can be selected properly in accordance with the purpose, by selecting the material of the coupling plate 3 and the size and shape of the boundary portion 3d.

The clip operating device 6 shown in FIG. 3 comprises a coil sheath 7 to be used as an operating member. The coil sheath 7 includes in the order from its distal end side a hollow coil pipe 7A and a hollow coil 7b fixed to the hollow coil pipe 7a. A tube sheath 8 is used as an introducing tube which covers the coil sheath 7. The coil sheath 7 and the tube sheath 8 are assembled relatively movable to each other. An operating wire 13 having a retainer 11 on its distal end side is advanceably and retreatably inserted through the coil sheath 7. A proximal end portion of the coil sheath 7 is coupled to a coil sheath operating portion 9, and a proximal end portion of the tube sheath 8 is coupled to a tube operating portion 10 which is provided on an outside periphery of the coil sheath operating portion 9. The proximal end side of the operating wire 13 is coupled to a slider 12.

The inside diameter of the coil pipe 7a is larger than the small-diameter portion 4c of the holding tube 4 so that the small-diameter portion 4c can be inserted in the coil pipe 7a, whereas the inside diameter of the coil pipe 7a is smaller than the large-diameter portion 4b so that the large-diameter portion 4b cannot be inserted in the coil pipe 7a. That is to say, a step portion between the small-diameter portion 4c and the large-diameter portion 4b abuts on the distal end of the coil pipe 7a. The outside diameter of the coil pipe 7a is approximately the same as the large-diameter portion 4b of the holding tube 4.

The retainer 11 is rod-shaped and provided on its distal end side with a recess 14. The recess 14 is provided on its bottom with a pin 15 which is vertical to the advancing and retreating direction of the operating wire 13. The pin 15 comprises a circular head portion 16 and a small-diameter portion 17 which has a smaller diameter than that of the head portion 16. The head portion 16 of the pin 15 is smaller than the large-diameter opening 3f of the coupling plate 3 as shown in FIG. 1(A) and is larger than the small-diameter opening 3g. Further, the small-diameter portion 17 of the pin 15 is smaller than the small-diameter opening 3g of the coupling plate 3.

The operation of the first embodiment will be described. When the clip unit 1 is attached to the clip operating device 6 as shown in FIG. 4, the slider 12 is pushed toward the distal end side, crusing the retainer 11 to protrude from the coil pipe 7a. After the pin 15 of the retainer 11 is fitted in the large-diameter opening 3f of the coupling plate 3 of the clip unit 1, the entire clip unit 1 is pulled toward the distal end side. Then, the head portion 16 of the pin 15 is engaged with the small-diameter opening 3g of the coupling plate 3. Further, by pulling the slider 12 toward the proximal end side, the retainer 11 is pulled in the coil sheath 7 and the small-diameter potion 4c of the holding tube 4 is inserted into the coil pipe 7a to complete the attachment of the clip unit 1.

Figure 5:
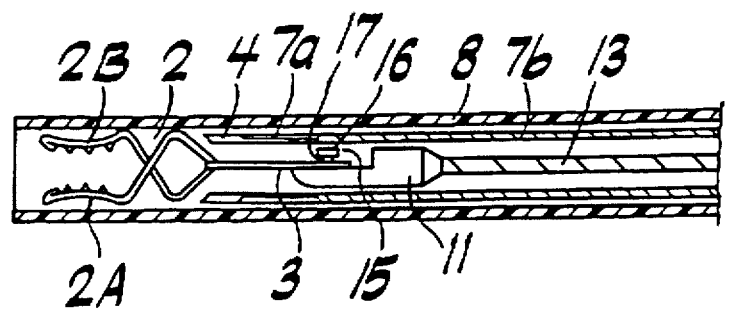
FIG. 5 is an illustration showing the state in which the clip is received in a distal end portion of a tube sheath.

Next, the tube sheath operating portion 10 is pushed toward the distal end side to cause the tube sheath 8 to protrude from the coil sheath 7 toward the distal end side so that the clip unit 1, which is already engaged with the retainer 11, is inserted into the tube sheath 8. With this operation, as shown in FIG. 5, the clip unit 1 is received in the hollow of the distal end portion of the tube sheath 8 with the arm portions 2A and 2B closed. In this state, the tube sheath 8 is introduced into a body cavity via a forceps channel of an endoscope that has been previously inserted into the body cavity. While the body cavity is observed via the endoscope, the distal end portion of the tube sheath 8 is guided to a part to be treated.

Figure 6:
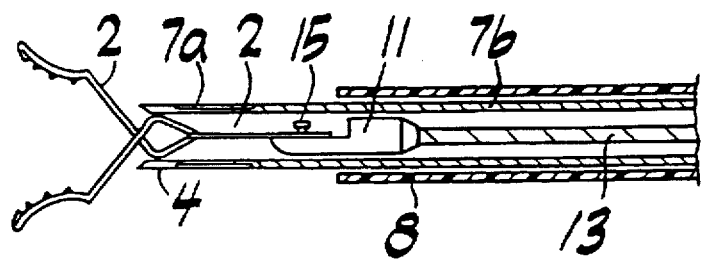
FIG. 6 is an illustration showing the state in which the clip is open after being exposed from the tube sheath.

Next, the tube sheath operating portion 10 is pulled toward the proximal end side to expose the clip unit 1 and the distal end portion of the coil sheath 7 from the tube sheath 8, as shown in FIG. 6. When the slider 12 is pulled toward the proximal end side to retreat the operating wire 13 toward the proximal end side, the oval-shaped portion of the proximal end portion 2d of the clip 2 is squeezed, because the width W1 of the oval-shaped portion of the proximal end portion 2d of the clip 2 is larger than the inside diameter of the holding tube 4. Then, as shown in FIG. 6, the arm portions 2A and 2B largely open outward.

Figure 1D:
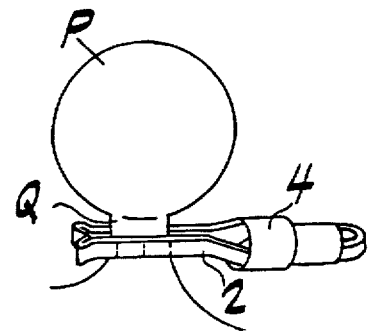
FIG. 1(D) is an illustration showing a state of the clip grasping a living tissue.

In this state, the clip 2 is guided so that it will grasp the object tissue. By further pulling the slider 12 toward the proximal end side, the operating wire 13 is retracted, and the arm portions 2A and 2B of the clip 2 are pulled in the holding tube 4. With this operation, the arm portions 2A and 2B are closed as shown in FIG. 1(C). For example, as shown in FIG. 1(D), when the arm portions 2A and 2B of the clip 2 grasp a stalk portion Q of a polyp P, the stalk portion can be grasped reliably by the entire bow-shaped portions 2a of the arm portions 2A and 2B owing to the elasticity of the bow-shaped portions 2a.

Figure 7:
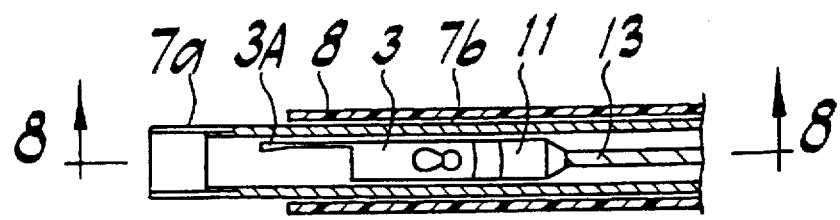
FIG. 7 is an illustration showing the state in which the hook portion of the coupling plate is deformed after the clip has grasped the tissue and has been left on the tissue.
Figure 8:
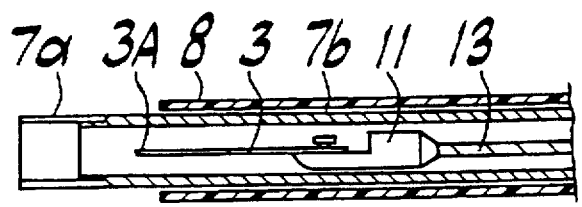
FIG. 8 is a sectional view from line B-B' in FIG. 7.

When the arm portions 2A and 2B of the clip 2 reliably grasp the living tissue and the slider 12 is further pulled toward the proximal end side to retract the operating wire 13, the hook portion 3A of the coupling plate 3 of the clip 2 is deformed and stretched as shown in FIGS. 7 and 8. The clip 2 disengages from the coupling plate 3, becomes detached from the clip operating device 6 and is left inside the body cavity, holding the tissue. Then, by using a conventional snare or the like, the end side of the tissue above the grasped portion is cut off and collected. Further, when ligating a varix such as an esophageal varix, the arm portions 2A and 2B of the clip 2 clip the varix. Then the clip 2 is left in the body cavity for several weeks, and the varix will disappear.

After disengaging the clip 2, the clip operating device 6 is removed from the force ps channel of the endoscope. Then, the slider 12 is pushed towards the distal end side to protrude the retainer 11 from the coil sheath 7, and the coupling plate 3 with the hook portion 3A stretched as shown in FIG. 2(B) is removed from the retainer 11. At this time, because the hook portion 3A of the coupling plate 3 is stretched as stated above, of the end portion 3e of the coupling plate 3 no longer exerts pressure against the inner wall of the holding tube 4. Therefore, the coupling plate 3 is not caught on the inner wall of the coil 7b and can be removed easily.

According to the first embodiment of this invention, because the end portion 3e of the hook portion 3A of the coupling plate 3 presses against the inner wall of the holding tube 4 to temporarily retain the respective members of the clip unit 1, the clip unit 1 can be assembled easily at a low cost. Further, the amount of the resilient force caused by the deformation of the hook portion 3A can be selected properly in accordance with the purpose, by selecting the material of the coupling plate 3 and the size and shape of the boundary portion 3d. Thus, the respective members of the clip unit 1 will not become separated by the handling of the clip device before the clip 2 is left on the living tissue.

Furthermore, after the clip 2 is left on the living tissue since the hook portion 3A of the coupling plate 3 is stretched to completely extinguish the pressure against the inner wall of the holding tube, the coupling plate 3 can easily be removed from the coil 7b. Moreover, since the living tissue can be grasped by the entire bow-shaped portions 2a owing to the elasticity of the bow-shaped portions 2a of the arm portions 2A and 2B, and since the inner side of the arm portions 2A and 2B are provided with a plurality of protrusion 2f, the arm portions 2A and 2B can securely grasp and ligate the tissue without slipping. Further, because the distal end portions of the clip 2 are formed obtusely, the clip 2 will not injure the tissue and can be used safely.

Figure 9A:
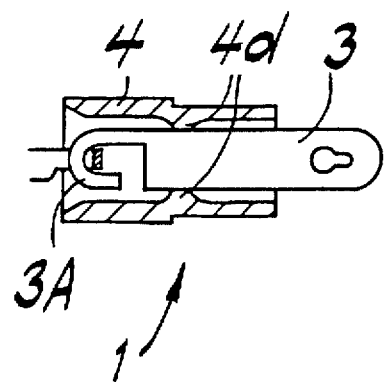
FIG. 9(A) is an illustration showing the shape of a clip of a second embodiment of this invention.
Figure 9B:
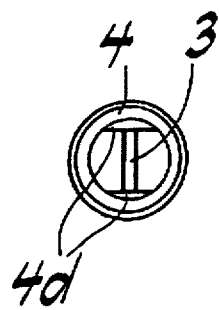
FIG. 9(B) is a rear view of the clip shown in FIG. 9(A).

Next, referring to FIGS. 9(A) and 9(B), a second embodiment of this invention will be described. In this embodiment, the inner wall of a holding tube 4 is provided with a pair of protruding portions 4d which protrude inward. The shape of a coupling plate 3 is approximately the same as that of the first embodiment. However, the width of the outer side of the hook portion 3A is the same as the width of the coupling plate 3, and the hook portion 3A has the same cross-sectional area along its entire length, which is different from the first embodiment. The remaining structures of the second embodiment not discussed above are the same as that of the first embodiment.

In the second embodiment, when the coupling plate 3 is inserted in the holding tube 4, it is pressed by the protruding portions 4d provided to the inner wall of the holding tube 4 and temporarily retained in the holding tube 4.

When the living tissue is sandwiched by the arm portions 2A and 2B of the clip 2 and the slider 12 is pulled toward the proximal end side to retract the operating wire 13, the hook portion 3A of the coupling plate 3 of the clip 2 is deformed and stretched, and the clip 2 separates from the clip operating device 6 and is left inside the body cavity, grasping the living tissue. When the operating wire 13 is further retracted to the proximal end side, the coupling plate 3 is disengaged from the protruding portions 4d provided in the holding tube 4 so that the pressure between the coupling plate 3 and the holding tube 4 disappears.

According to the second embodiment, the shape of the coupling plate 3 can be simpler than that of the first embodiment. Further, the amount of the pressure between the coupling plate 3 and the inner wall of the holding tube 4 can be selected properly by selecting the height of the protruding portions 4d and the width of the coupling plate 3. Other functions and results are the same as those of the first embodiment.

Figure 10:
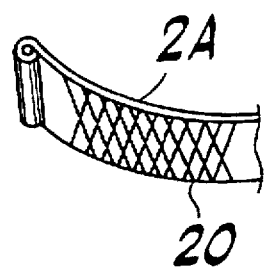
FIG. 10 is an illustration showing the shape of an arm portion of a clip of a third embodiment of this invention.

Referring to FIG. 10, a third embodiment of this invention will be described. This embodiment is different from the first embodiment in that the distal end portions of the arm portions 2A and 2B of the clip 2 are curled to be obtuse, and the inner sides of the arm portions 2A and 2B are provided with ridges resembling a file instead of protrusions. The functions and results of the third embodiment are the same as those of the first embodiment. Thus its description will be omitted.

As described above, because the clip device of this invention is designed such that the coupling member can be held temporarily by the inner wall of the clip squeezing ring, the clip unit can be assembled easily at a low cost. Further, since the amount of the force for holding the squeezing ring and the coupling member can be selected properly by selecting the inside shape of the clip squeezing ring and the material and shape of the coupling member, the coupling member and the clip squeezing ring will not become separated by the handling of the clip device before the clip is left on the living tissue. Further, after the clip is left on the living tissue since the pressure between the coupling member and the inner wall of the squeezing ring has completely disappeared, the coupling member can be removed easily from the clip device. Furthermore, since the living tissue can be grasped by the entire bow-shaped portions owing to the elasticity of the bow-shaped portions provided to the clip, and since the inner sides of the arm portions of the clip are provided with a means for increasing the friction between the inner sides of the arm portions and the living tissue, the arm portions can reliably grasp and ligate the tissue without slipping. Moreover, because the distal end portions of the clip are formed obtusely, the clip will not injure the tissue and can be used safely.

Further widely different embodiments of this invention may be made without departing from the spirit and scope of this invention. This invention will not be limited to the specific embodiments thereof except as defined in the appended claims.

What is claimed is:

1. A clip device for a living tissue in a body cavity, comprising:

an introducing tube insertable into the body cavity;

an operating member advanceably and retreatably inserted into the introducing tube and having a distal end portion;

an operating wire advanceably and retreatably inserted into the operating member and having a distal end portion and a retainer attached to the distal end portion;

a clip having a proximal end portion and a pair of arm portions extending from the proximal end portion and provided with a tendency to open;

a clip squeezing ring removably attached to the distal end portion of the operating member for closing the arm portions of the clip by fitting to the arm portions of the clip;

a coupling member insertable into the clip squeezing ring, the coupling member being removably engaged with the retainer and having a hook portion to be engaged with the proximal end portion of the clip; and holding means for holding the coupling member inside the clip squeezing ring by an elastic deformation of the coupling member such that the coupling member can be removed from the clip squeezing ring when the operating wire is retreated.

2. A clip unit for a living tissue in a body cavity to be used with a clip operating device having an introducing tube insertable into the body cavity, an operating member advanceably and retreatably inserted into the introducing tube and having a distal end portion, and an operating wire advanceably and retreatably inserted into the operating member and having a distal end portion and a retainer attached to the distal end portion, the clip unit comprising:

a clip having a proximal end portion and a pair of arm portions extending from the proximal end portion and provided with a tendency to open;

a clip squeezing ring removably attachable to the distal end portion of the operating member of the clip operating device for closing the arm portions of the clip by fitting to the arm portions of the clip;

a coupling member insertable into the clip squeezing ring, the coupling member being removably engagable with the retainer of the operating wire of the clip operating device and having a hook portion to be engaged with the proximal end portion of the clip; and holding means for holding the coupling member inside the clip squeezing ring by an elastic deformation of the coupling member such that the coupling member can be removed from the clip squeezing ring when the coupling member is retreated.

3. The clip unit according to claim 2, wherein the holding means is provided to the coupling member.

4. The clip unit according to claim 3, wherein the clip squeezing ring comprises an inner wall having an inside diameter, and wherein the holding means is an elastic portion for pressing against the inner wall of the clip squeezing ring so as to be temporarily retained therein.

5. The clip unit according to claim 4, wherein the elastic portion is formed by a part of the hook portion of the coupling member and the width of the coupling member at the elastic portion is larger than the inside diameter of the clip squeezing ring.

6. The clip unit according to claim 2, wherein the holding means is provided to the clip squeezing ring.

7. The clip unit according to claim 6, wherein the clip squeezing ring comprises an inner wall, and the holding means comprises a protrusion provided to the inner wall of the clip squeezing ring for pressing against the coupling member.

8. The clip unit according to claim 2, wherein a part of the hook portion has a small cross-sectional area.

9. The clip unit according to claim 2, wherein at least one of the arm portions is bent inward so as to be bow-shaped.

10. The clip unit according to claim 2, wherein at least one of the arm portions has an inner side provided with a friction increasing structure for increasing a friction between the inner side of the arm portion and the living tissue.

11. The clip unit according to claim 10, wherein the friction increasing structure comprises a protrusion.

12. The clip unit according to claim 10, wherein the friction increasing structure comprises ridges.

13. The clip unit according to claim 2, wherein the arm portion has a distal end portion which is folded back.

14. The clip unit according to claim 2, wherein the arm portion has a distal end portion which is curled.

* * * * *

UNITED STATES PATENT AND TRADEMARK OFFICE
CERTIFICATE OF CORRECTION

PATENT NO. : 5,766,189
DATED : June 16, 1998
INVENTOR(S) : Kiyotaka Matsuno

It is certified that error appears in the above-identified patent and that said Letters Patent is hereby corrected as shown below:

Abstract,
Line 14, delete "And" and change "a" to -- A --.
Line 18, change "clip;" to -- clip. --.
Line 19, before "holding" insert -- A --.
Line 24, after "with" insert -- a --.
Line 25, before "friction" insert -- the --.

Column 1,
Line 51, delete the comma after "tissue".
Line 66, change "portion;" to -- portion. --.

Column 2,
Line 3, delete the comma after "includes"
Line 18, insert -- a -- after "increasing" at end of line.

Column 3,
Line 4, after "2" insert a comma.

Column 4,
Line 2, delete the period after "unit" and insert -- 2. --.
Line 30, insert a comma after "3A".
Line 39, change "7A" to -- 7a --.

Column 5,
Line 11, change "crusing" to -- causing --.
Line 19, change "potion" to -- portion --.
Line 64, after "6" insert a comma.
Line 65, delete the comma after "cavity".

Column 6,
Line 5, change "6is" to -- 6 is --.
Line 6, change "force ps" to -- forceps --.
Line 28, insert a comma after "tissue".

UNITED STATES PATENT AND TRADEMARK OFFICE
CERTIFICATE OF CORRECTION

PATENT NO. : 5,766,189
DATED : June 16, 1998
INVENTOR(S) : Kiyotaka Matsuno

It is certified that error appears in the above-identified patent and that said Letters Patent is hereby corrected as shown below:

Column 7,
Line 28, insert a comma after "tissue".

Column 8,
Line 40, after "and" insert -- wherein --.

Signed and Sealed this

Eighteenth Day of September, 2001

*Attest:*

NICHOLAS P. GODICI
*Attesting Officer*     *Acting Director of the United States Patent and Trademark Office*